United States Patent
Kato et al.

(10) Patent No.: US 11,433,005 B2
(45) Date of Patent: Sep. 6, 2022

(54) DENTAL FILLING MATERIAL AND DENTAL POLYMERIZABLE COMPOSITION

(71) Applicant: GC Corporation, Shizuoka (JP)

(72) Inventors: Hiroki Kato, Tokyo (JP); Satoshi Jin, Tokyo (JP)

(73) Assignee: GC CORPORATION, Shizuoka (JP)

( * ) Notice: Subject to any disclaimer, the term of this patent is extended or adjusted under 35 U.S.C. 154(b) by 0 days.

(21) Appl. No.: 17/040,708

(22) PCT Filed: Dec. 4, 2018

(86) PCT No.: PCT/JP2018/044571
§ 371 (c)(1),
(2) Date: Sep. 23, 2020

(87) PCT Pub. No.: WO2019/187351
PCT Pub. Date: Oct. 3, 2019

(65) Prior Publication Data
US 2021/0007939 A1 Jan. 14, 2021

(30) Foreign Application Priority Data
Mar. 29, 2018 (JP) .............................. JP2018-065671

(51) Int. Cl.
*A61K 6/887* (2020.01)
*A61K 6/836* (2020.01)

(52) U.S. Cl.
CPC .............. *A61K 6/887* (2020.01); *A61K 6/836* (2020.01)

(58) Field of Classification Search
CPC .................................................... A61K 6/887
See application file for complete search history.

(56) References Cited

U.S. PATENT DOCUMENTS

| 2004/0067359 | A1 | 4/2004 | Hirasawa et al. |
| 2005/0250868 | A1* | 11/2005 | Suzuki ................... A61K 6/891 522/25 |
| 2006/0004121 | A1 | 1/2006 | Ding et al. |
| 2011/0189632 | A1* | 8/2011 | Frances ................... A61K 6/896 433/172 |
| 2013/0059941 | A1 | 3/2013 | Craig et al. |

FOREIGN PATENT DOCUMENTS

| JP | 2003-095837 | 4/2003 |
| JP | 2007-161510 | 6/2007 |
| JP | 2007-314484 | 12/2007 |
| JP | 2015-500302 | 1/2015 |
| WO | 2013/087223 | 6/2013 |

OTHER PUBLICATIONS

International Search Report for PCT/JP2018/044571 dated Feb. 12, 2019.
Stansbury, Jeffrey W. et al., Epoxy-brush Modified Fillers for Dental Composites, Polymer Preprints, Aug. 2004, vol. 45, No. 2, pp. 341-342, ISSN 0032-3934.
Ding, Xingzhe et al., Polymer-brush Modified Fillers for Dental Composites, Polymer Preprints, Aug. 2004, vol. 45, No. 2, pp. 339-340, ISSN 0032-3934.

* cited by examiner

*Primary Examiner* — Michael F Pepitone
(74) *Attorney, Agent, or Firm* — IPUSA, PLLC

(57) ABSTRACT

According to one aspect of the present invention, a dental filling material is manufactured by surface-treating an inorganic filling material with a silane coupling agent having an epoxy group and then by causing a ring-opening reaction with a composition containing an epoxide having a (meth)acryloyl group.

7 Claims, No Drawings

DENTAL FILLING MATERIAL AND DENTAL POLYMERIZABLE COMPOSITION

CROSS-REFERENCE TO RELATED APPLICATIONS

This application is a national stage filing under 35 U.S.C. 371 of International Patent Application No. PCT/JP2018/044571, filed on Dec. 4, 2018, which claims priority to Japanese Patent Application No. 2018-065671, filed on Mar. 29, 2018.

TECHNICAL FIELD

The present invention relates to a dental filling material and a dental polymerizable composition.

BACKGROUND ART

Conventionally, an inorganic filling material such as silica or barium glass is mixed into a dental restorative material in order to enhance the mechanical strength of a hardened body.

However, a dental restorative material, into which an inorganic filling material is mixed, is insufficient in the smoothness of a hardened body.

For example, Patent Document 1 discloses a dental filling material that is manufactured by surface-treating an inorganic filling material with a silane coupling agent having a methacryloyl group and then causing a reaction with a (meth)acrylate.

PRIOR ART DOCUMENTS

Patent Documents

[Patent Document 1] Japanese Laid-open Patent Publication No. 2007-314484

DISCLOSURE OF THE INVENTION

Problem to be Solved by the Invention

However, there is a problem that the operability of a dental restorative material, the smoothness and the flexural strength of a hardened body of the dental restorative material cannot be achieved at the same time.

One aspect of the present invention has an object to provide a dental filling material that enables to achieve the operability of a dental restorative material and the smoothness and the flexural strength of a hardened body of the dental restorative material at the same time.

Means for Solving the Problem

According to one aspect of the present invention, a dental filling material is manufactured by surface-treating an inorganic filling material with a silane coupling agent having an epoxy group and then by causing a ring-opening reaction with a composition containing an epoxide having a (meth)acryloyl group.

According to another aspect of the present invention, a dental filling material is manufactured by causing a silane coupling agent having an epoxy group, a composition containing an epoxide having a (meth)acryloyl group, and an inorganic filling material to react.

Effects of the Invention

One aspect of the present invention provides a dental filling material that enables to achieve the operability of a dental restorative material and the smoothness and the flexural strength of a hardened body of the dental restorative material at the same time.

EMBODIMENT FOR CARRYING OUT THE INVENTION

In the following, an embodiment for carrying out the present invention will be described. The present invention is not limited to the following embodiment, and various modifications and substitutions can be made to the following embodiment without departing from the scope of the claims.

Method of Manufacturing Dental Filling Material

In the following, a method of manufacturing a dental filling material according to the present embodiment will be described.

First, an inorganic filling material is surface-treated with a silane coupling agent having an epoxy group to introduce the epoxy group on the surface of the inorganic filling material.

Examples of the material constituting the inorganic filling material include silica, barium glass, fluoroaluminosilicate glass, and the like.

The average particle size of the inorganic filling material is preferably in the range of 0.005 μm to 5 μm, and is more preferably in the range of 0.05 μm to 0.5 μm.

It is preferable that the silane coupling agent having an epoxy group is a compound that is represented by the following general chemical formula (1).

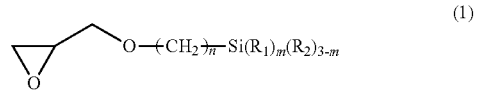

(1)

(Where $R_1$ is an alkoxy group having 1 to 6 carbon atoms, an isocyanate group, or a chlorine atom, $R_2$ is a hydrocarbon group having 1 to 6 carbon atoms, m is an integer of 1 to 3, and n is an integer of 1 to 20.)

Examples of the silane coupling agent having an epoxy group include 3-glycidyloxypropyltrimethoxysilane and the like.

It should be noted that the silane coupling agent may have two or more epoxy groups.

A known surface-treating method can be used when surface-treating the inorganic filling material with the silane coupling agent having an epoxy group.

Next, the inorganic filling material having the epoxy group introduced to the surface is subject to a ring-opening reaction with an epoxy composition containing an epoxide having a (meth)acryloyl group. Thereby, it is possible to obtain a dental filling material. At this time, on the surface of the obtained dental filling material, the (meth)acryloyl group derived from the epoxide containing the (meth)acryloyl group remains.

Here, in order to adjust the particle sizes to be suitable for being mixed in a dental polymerizable composition, the dental filling material may be pulverized, if necessary.

A known pulverizer can be used when pulverizing the dental filling material.

In the specification and claims of the present application, a (meth)acryloyl group means a methacryloyl group and/or an acryloyl group.

Examples of the epoxide having a (meth)acryloyl group include a methacrylic acid adduct of bisphenol A diglycidyl ether, a methacrylic acid adduct of bisphenol E diglycidyl ether, 3,4-epoxycyclohexylmethylmethacrylate, and the like.

It is preferable that the epoxide having a (meth)acryloyl group is a compound that is represented by the following general chemical formula (2).

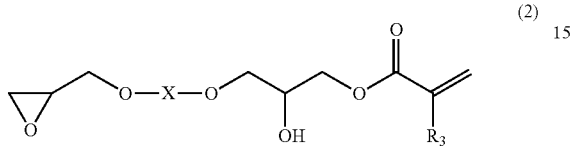

(2)

(Where $R_3$ is a hydrogen atom or a methyl group and X is a divalent organic group).

Specific examples of the divalent organic group in X are indicated below.

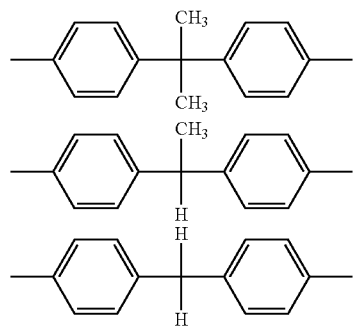

Examples of commercially available epoxides having a (meth)acryloyl group include BAEM-50, BEEM-50 (manufactured by KSM Corporation), Cyclomer M100 (manufactured by Daicel Corporation), and the like.

It should be noted that the epoxide having a (meth) acryloyl group may have two or more (meth)acryloyl groups and/or epoxy groups.

Here, the epoxy composition is not particularly limited as long as it is possible to cause a ring-opening reaction with an epoxy group introduced to the surface of the inorganic filling material.

It is preferable that the epoxy composition contains a known ring-opening reaction initiator.

The ring-opening reaction initiator is not particularly limited as long as it can open an epoxy group. Examples of the ring-opening reaction initiator include amines (such as primary, secondary, tertiary amines, aromatic amines, amine complexes), polyimide resins, imidazoles, polymercaptans, acid anhydrides, organic hydrazides, and the like. In particular, N,N-diethyl-1,3-diaminopropane, 2,2'-diaminodiethylamine, bis(4-aminophenyl)sulfone, phthalic anhydride, and the like are preferable.

The epoxy composition may further contain an epoxide not having a (meth)acryloyl group. This makes it easier to make a dental filling material.

It should be noted that the epoxide not having a (meth) acryloyl group may include two or more epoxy groups.

Examples of the epoxide not having a (meth)acryloyl group include neopentylglycoldiglycidylether, 2,2-bis(4-glycidyloxyphenylphenyl)propane, and the like.

In a case in which an inorganic filling material having a silanol group on the surface is used, the surface of a dental filling material has a structure that is represented by the following general chemical formula, for example.

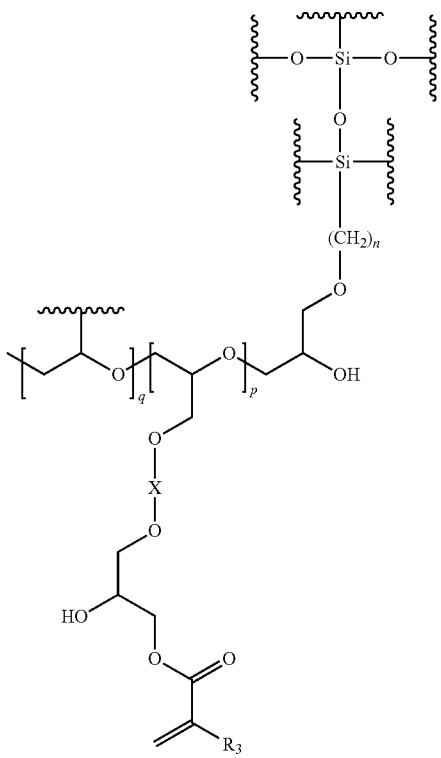

(Where p and q are respectively the degree of polymerization of an epoxide having a (meth)acryloyl group and the degree of polymerization of an epoxide not having a (meth) acryloyl group, and n, $R_3$, and X are similar to those in the general formulas (1) and (2)). Here, in a copolymer of an epoxide having a (meth)acryloyl group and an epoxide not having a (meth)acryloyl group, the bonding order of the epoxide having a (meth)acryloyl group and the epoxide not having a (meth)acryloyl group is not particularly limited.

Examples of a copolymer of an epoxide having a (meth) acryloyl group and an epoxide not having a (meth)acryloyl group include a random copolymer, an alternating copolymer, a block copolymer, and the like.

It should be noted that when manufacturing the dental filling material, it may be possible to cause a silane coupling agent having an epoxy group, a composition containing an epoxide having a (meth)acryloyl group, and an inorganic filling material to react.

Also, as needed, the dental filling material may be surface-treated with a silane coupling agent having a (meth) acryloyl group to further introduce the (meth)acryloyl group onto the surface of the inorganic filling material. This further enhances the flexural strength of a hardened body of the dental polymerizable composition, which will be described later below.

Dental Filling Material

A dental filling material according to the present embodiment is manufactured by the method of manufacturing a dental filling material according to the present embodiment.

The content of an inorganic filling material in the dental filling material is preferably in the range of 40% to 95% by mass and is more preferably in the range of 60% and 80% by mass. When the content of the inorganic filling material in the dental filling material is greater than or equal to 20% by mass, the flexural strength of a hardened body of a dental polymerizable composition described below is enhanced, and when the content is less than or equal to 95% by mass, the operability of the dental polymerizable composition is enhanced.

In a case in which the dental filling material according to the present embodiment is surface-treated with a silane coupling agent having a (meth)acryloyl group, the content of the silane coupling agent having a (meth)acryloyl group in the dental filling material is preferably in the range of 0.1% to 20% by mass, and is more preferably in the range of 0.5% to 10% by mass. When the content of the silane coupling agent having a (meth)acryloyl group in the dental filling material is greater than or equal to 0.1% by mass and less than or equal to 20% by mass, the flexural strength of a hardened body of a dental polymerizable composition is further enhanced.

Dental Polymerizable Composition

A dental polymerizable composition according to the present embodiment includes a dental filling material according to the present embodiment and a (meth)acrylate, and may further include, as needed, a polymerization initiator, a filling material other than the dental filling material according to the present embodiment, a polymerization inhibitor, an antioxidant, an ultraviolet absorber, a pigment, and the like.

In the specification and claims of the present application, a (meth)acrylate means a compound having one or more (meth)acryloyloxy groups (for example, a monomer or a macromonomer).

(Meth)acrylate

Examples of the (meth)acrylate include, but are not limited to, methyl (meth)acrylate, ethyl (meth)acrylate, isopropyl (meth)acrylate, n-butyl (meth)acrylate, isobutyl (meth)acrylate, hydroxypropyl (meth)acrylate, tetrahydrofurfuryl (meth)acrylate, glycidyl (meth)acrylate, 2-hydroxyethyl (meth)acrylate, 2-hydroxypropyl (meth)acrylate, 3-hydroxypropyl (meth)acrylate, 2-methoxyethyl (meth)acrylate, 2-ethoxyethyl (meth)acrylate, 2-methyihexyl (meth)acrylate, 2-ethylhexyl (meth)acrylate, 2-ethylhexyl (meth)acrylate, benzyl (meth)acrylate, 2-hydroxy-1,3-di(meth)acryloyloxypropane, ethylene glycol di(meth)acrylate, diethylene glycol di(meth)acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylolethane tri(meth)acrylate, pentaerythritol tri(meth)acrylate, trimethylolmethane tri(meth)acrylate, pentaerythritol tetra(meth)acrylate, polybutylene glycol di(meth)acrylate, bisphenol A diglycidyl (meth)acrylate, di-2-(meth)acryloyloxyethyl-2,2,4-trimethylhexamethylenedicarbamate, 1,3,5-tris[1,3-bis{(meth)acryloyloxy}-2-propoxycarbonylaminohexane]-1,3,5-(1H,3H,5H)triazine-2,4,6-trione, 2,2-bis-4-(3-(meth)acryloyloxy-2-hydroxypropyl)-phenylpropane, a (meth)acrylate of a urethane oligomer consisting of 2,2'-bis(4-hydroxycyclohexyl)propane, 2-oxypanone, hexamethylene diisocyanate, and 2-hydroxyethyl (meth)acrylate, a (meth)acrylate of a urethane oligomer consisting of 1,3-butanediol, hexamethylene diisocyanate, and 2-hydroxyethyl (meth)acrylate.

The content of the (meth)acrylate in the dental polymerizable composition is preferably in the range of 0.5% to 70% by mass, and is more preferably in the range of 10% to 60% by mass. When the content of the (meth)acrylate in the dental polymerizable composition is greater than or equal to 0.5% by mass, the mechanical strength of a hardened body of the dental polymerizable composition is enhanced, and when the content is less than or equal to 70% by mass, the content of other components can be secured and the performance as a dental polymerizable composition is enhanced.

A silane coupling agent having a (meth)acryloyl group can also be used as the (meth)acrylate.

Examples of the silane coupling agent having a (meth)acryloyl group may include, but are not particularly limited to, 3-(meth)acryloyloxypropyltrimethoxysilane, 3-(meth)acryloyloxypropylmethyldimethoxysilane, 3-(meth)acryloyloxypropyltriethoxysilane, 3-(meth)acryloyloxypropylethyldiethoxysilane, 3-(meth)acryloyloxypropylmethyldiethoxysilane, 2-(meth)acryloyloxyethoxypropyltrimethoxysilane, and the like, and two or more kinds of these may be used in combination as the silane coupling agent having a (meth)acryloyl group.

The content of the silane coupling agent having a (meth)acryloyl group in the dental polymerizable composition is preferably in the range of 0.5% to 10% by mass, and is more preferably in the range of 1.5% to 5% by mass. When the content of the silane coupling agent having a (meth)acryloyl group in the dental polymerizable composition is greater than or equal to 0.5% by mass, the mechanical strength of a hardened body of the dental polymerizable composition is enhanced, and when the content is less than or equal to 10% by mass, the content of other components can be secured and the performance as a dental polymerizable composition is enhanced.

Polymerization Initiator

The dental polymerizable composition according to the present embodiment may further include a polymerization initiator.

As the polymerization initiator, a chemical polymerization initiator and/or a photopolymerization initiator can be used, and a photopolymerization initiator is preferably used.

Photopolymerization Initiator

Examples of the photopolymerization initiator include, but are not particularly limited to, a ketone-based compound, an α-diketone-based compound, a ketal-based compound, an anthraquinone-based compound, a thioxanthone-based compound, a benzoin alkyl ether-based compound, an acylphosphine oxide-based compound, and the like.

Examples of the ketone-based compound include benzophenone, bis(4-dimethylaminophenyl)ketone, 4,4'-bis(diethylamino)benzophenone, and the like.

Examples of the α-diketone-based compound include camphorquinone, benzyl, diacetyl, acenaphthenequinone, 9,10-phenanthrequinone, and the like.

Examples of the ketal-based compound include benzyl ketal, diacetyl ketal, benzyl dimethyl ketal, benzyl diethyl ketal, benzyl bis(β-phenylethyl)ketal, benzyl bis(2-methoxyethyl)ketal, 4,4'-dimethyl(benzyl dimethyl ketal), and the like.

Examples of the anthraquinone-based compound include anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, and the like.

Examples of the thioxanthone-based compound include thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10, 10-dioxide, thioxanthone-10-oxide, 2-ethylthioxanthone, 2-chlorothioxanthone, 2-hydroxy-3-(3,4-dimethyl-9-oxo-9H-thioxanthen-2-yloxy)-N,N,N-trimethyl-1-propan-aminium chloride.

Examples of the benzoin alkyl ether-based compound include benzoin methyl ether, benzoin ethyl ether, benzoin propyl ether, benzoin isobutyl ether, and the like.

Examples of the acylphosphine oxide-based compound include 2,4,6-trimethylbenzoyl diphenyl phosphine oxide, 2,4,6-trimethoxybenzoyl diphenyl phosphine oxide, 2,6-dimethylbenzoyl diphenyl phosphine oxide, 2,6-dimethoxybenzoyl diphenyl phosphine oxide, and the like.

The content of the photopolymerization initiator in the dental polymerizable composition is preferably in the range of 0.1% to 10% by mass, and is more preferably in the range of 0.2% to 5% by mass. When the content of the photopolymerization initiator in the dental polymerizable composition is greater than or equal to 0.1% by mass, the mechanical strength of a hardened body of the dental polymerizable composition is enhanced, and when the content is less than or equal to 10% by mass, the preservation stability of the dental polymerizable composition is enhanced.

It should be noted that in a case in which a photopolymerization initiator is used as the polymerization initiator, a photopolymerization accelerator may be used in combination.

Photopolymerization Accelerator

Examples of the photopolymerization accelerator may include, but are not particularly limited to, tertiary amines such as N,N-dimethyl-p-toluidine, triethanolamine, tolyldiethanolamine, methyl 4-dimethylaminobenzoate, ethyl 4-dimethylaminobenzoate, and isoamyl 4-dimethylaminobenzoate, barbituric acid, derivatives pf barbituric acid such as 1,3-dimethyl barbituric acid, 1,3,5-trimethyl barbituric acid, 1,3,5-triethyl barbituric acid, 5-butyl barbituric acid, 1-benzyl-5-phenyl barbituric acid, and 1-cyclohexyl-5-ethyl barbituric acid, and the like, and two or more kinds of these may be used in combination as the photopolymerization accelerator.

The content of the photopolymerization accelerator in the dental polymerizable composition is preferably in the range of 0.1% to 5% by mass, and is more preferably in the range of 0.2% to 1% by mass. When the content of the photopolymerization promoter in the dental polymerizable composition is greater than or equal to 0.1% by mass and less than or equal to 5% by mass, the polymerization efficiency of the dental polymerizable composition is further enhanced.

Filling Material Other Than Dental Filling Material According to the Present Embodiment As a filling material other than the dental filling material according to the present embodiment, it is possible to use an organic filling material and/or an inorganic filling material, and it is preferable to use an inorganic filling material.

Examples of the inorganic filling material may include, but are not particularly limited to, a silica powder, an alumina powder, a glass powder (for example, a barium glass powder, a fluoroaluminosilicate glass powder), and the like, and two or more kinds of these may be used in combination as the inorganic filling material.

The inorganic filling material may be surface-treated with a silane coupling agent as needed.

The content of the filling material described above in the dental polymerizable composition is preferably in the range of 0.1% to 20% by mass, and is more preferably in the range of 0.5% to 10% by mass. When the content of the filling material described above in the dental polymerizable composition is greater than or equal to 0.1% and less than or equal to 20% by mass, the mechanical strength of a hardened body of the dental polymerizable composition is further enhanced.

Use of Dental Polymerizable Composition

Examples of a use of the dental polymerizable composition according to the present embodiment include, but are not limited to, a dental restorative material, a dental cement, and the like. Among these, a dental restorative is preferable.

EXAMPLES

In the following, Examples of the present invention will be described, but the present invention is not limited to Examples. It should be noted that "parts" means parts by mass.

Example 1

Preparation of Epoxy Composition

By mixing 50 parts of BAEM-50 (manufactured by KSM. Co., Ltd) as an epoxide having a methacryloyl group, 50 parts of neopentyl glycol diglycidyl ether 1500NP (manufactured by KYOEISYA CHEMICAL Co., Ltd.) as an epoxide not having a methacryloyl group, and 7 parts of N,N-diethyl-1,3-diaminopropane (DEDAP) as a ring-opening reaction initiator, an epoxy composition was obtained.

Preparation of Filling Material 3

To 100 parts of a fluoroaluminosilicate glass filler having an average particle size of 0.4 μm as an inorganic filling material, a mixture liquid of 5 parts of 3-glycidyloxypropyltrimethoxysilane (GPS) as a silane coupling agent having an epoxy group, 1 part of distilled water, and 0.1 parts of acetic acid was added, and the mixture was kneaded for 30 minutes, and then dried at 80° C. for three hours to obtain a filling material 1 where the epoxy group was introduced to the surface.

75 parts of the filling material 1 and 25 parts of the epoxy composition were kneaded to obtain a paste for filling material.

The paste for filling material was heated at 80° C. in the atmosphere for two days to cause a ring-opening reaction, and then pulverized to obtain a filling material 2 with an average particle size of 10 μm.

To 100 parts of the filling material 2, a mixture liquid of 10 parts of 3-methacryloyloxypropyltrimethoxysilane (MPS) as a silane coupling agent having a methacryloyl group, 2 parts of distilled water, and 0.2 parts of acetic acid was added, and the mixture was kneaded for 30 minutes, and then dried at 80° C. for three hours to obtain a filling material 3.

Preparation of Filling Material 4

To 100 parts of a fluoroaluminosilicate glass filler having an average particle size of 0.4 µm, a mixture liquid of 5 parts of 3-methacryloyloxypropyltrimethoxysilane (MPS), 1 part of distilled water, and 0.1 parts of acetic acid was added, and the mixture was kneaded for 30 minutes, and then dried at 80° C. for three hours to obtain a filling material 4.

Preparation of Monomer Composition

By mixing 50 parts of 2,2-bis[4-(3-methacryloyloxy-2-hydroxypropoxy)phenyl]propane (Bis-GMA), 50 parts of neopentyl glycol dimethacrylate (NPG), 0.5 parts of (±)-camphorquinone (CQ) as a photopolymerization initiator, and 0.5 parts of 4-(N,N-dimethylamino)ethyl benzoate (DMABE) as a photopolymerization accelerator, a monomer composition was obtained.

Preparation of Dental Restorative Material 40 parts of the filling material 3, 20 parts of the monomer composition, 1 part of AEROSIL (registered trade mark) R972 (manufactured by NIPPON AEROSIL Co., Ltd) having an average particle size of 0.016 µm, and 39 parts of the filling material 4 were kneaded and then defoamed under vacuum to obtain a dental restorative material in a paste state.

Examples 2 and 3

With the exception of changing that the amount of MPS added to 1 part and 15 parts respectively when preparing the filling material 3, dental restorative materials were obtained similarly to Example 1.

Example 4

With the exception of using 8-glycidyloxyoctyltrimethoxysilane (GOS) was as a silane coupling agent having an epoxy group when preparing the filling material 1, a dental restorative material was obtained similarly to Example 1.

Example 5

Preparation of Epoxy Composition

By mixing 30 parts of BAEM-50 (manufactured by KSM. Co., Ltd) as an epoxide having a methacryloyl group, 20 parts of 2,2-bis(4-glycidyloxyphenylphenyl)propane (Bis-GPP) and 50 parts of neopentyl glycol diglycidyl ether 1500NP (manufactured by KYOEISYA CHEMICAL Co., Ltd.) as an epoxide not having a methacryloyl group, and 7 parts of N,N-diethyl-1,3-diaminopropane (DEDAP) as a ring-opening reaction initiator, an epoxy composition was obtained.

With the exception of using the obtained epoxy composition, a dental restorative material was obtained similarly to Example 1.

Example 6

Preparation of Epoxy Composition

By mixing 10 parts of BAEM-50 (manufactured by KSM. Co., Ltd) as an epoxide having a methacryloyl group, 40 parts of 2,2-bis(4-glycidyloxyphenylphenyl)propane (Bis-GPP) and 50 parts of neopentyl glycol diglycidyl ether 1500NP (manufactured by KYOEISYA CHEMICAL Co., Ltd.) as an epoxide not having a methacryloyl group, and 7 parts of N,N-diethyl-1,3-diaminopropane (DEDAP) as a ring-opening reaction initiator, an epoxy composition was obtained.

With the exception of using the obtained epoxy composition, a dental restorative material was obtained similarly to Example 1.

Example 7

With the exception of changing the amount of inorganic filling material added to 80 parts when preparing the filling material 1 and changing the amount of epoxy composition added to 15 parts when preparing the paste for filling material, a dental restorative material was obtained similarly to Example 1.

Example 8

With the exception of using a fluoroaluminosilicate glass filler having an average particle size of 1.0 µm as an inorganic filling material when preparing the filling material 1, a dental restorative was obtained similarly to Example 1.

Example 9

With the exception of using BEEM-50 (manufactured by KSM. Co., Ltd) as an epoxide having a methacryloyl group when preparing the epoxy composition, a dental restorative was obtained similarly to Example 5.

Example 10

Preparation of Filling Material 2'

71.4 parts of a fluoroaluminosilicate glass filler having an average particle size of 0.4 µm, 3.6 parts of 3-glycidyloxypropyltrimethoxysilane (GPS), and 25 parts of the epoxy composition were kneaded to obtain a paste for filling material.

The paste for filling material was heated at 80° C. in the atmosphere for two days to cause a ring-opening reaction, and then pulverized to obtain a filling material 2' with an average particle size of 10 µm.

With the exception of using the filling material 2' instead of the filling material 2, a dental restorative material was obtained similarly to Example 1.

Comparative Example 1

Preparation of Epoxy Composition

By mixing 50 parts of 2,2-bis(4-glycidyloxyphenylphenyl)propane (Bis-GPP) and 50 parts of neopentyl glycol diglycidyl ether 1500NP (manufactured by KYOEISYA CHEMICAL Co., Ltd.) as an epoxide not having a methacryloyl group, and 7 parts of N,N-diethyl-1,3-diaminopropane (DEDAP) as a ring-opening reaction initiator, an epoxy composition was obtained.

With the exception of using the obtained epoxy composition, a dental restorative material was obtained similarly to Example 1.

Comparative Example 2

Preparation of Monomer Composition

By mixing 50 parts of 2,2-bis[4-(3-methacryloyloxy-2-hydroxypropoxy)phenyl]propane (Bis-GMA), 50 parts of neopentyl glycol dimethacrylate (NPG), and 0.5 parts of 2,2'-azobis(isobutyronitrile) (AIBN) as a polymerization initiator, a monomer composition was obtained.

Preparation of Filling Material 2"

75 parts of the filling material 1 and 25 parts of the monomer composition were kneaded to obtain a paste for filling material.

The paste for filling material was heated at 80° C. in the atmosphere for two days to be polymerized, and then pulverized to obtain a filling material 2" with an average particle size of 10 μm.

With the exception of using the filling material 2" instead of the filling material 2, a dental restorative material was obtained similarly to Example 3.

Next, the operability of each dental restorative material and the flexural strength and the smoothness of a hardened body of each dental restorative material were evaluated.

Operability

Under conditions of 37° C. and 100% RH, by filling a model of a first-class cavity with the dental restorative material, the operability was evaluated. It should be noted that the operability was determined based on the following criteria.

Excellent: when the dental restorative material has particularly low stickiness or dryness and filling is particularly easy Good: when the dental restorative material has low stickiness or dryness and filling is easy Unacceptable: when the dental restorative material is very sticky or dry and filling is not easy Flexural Strength of Hardened Body A cuboid mold of 25 mm×2 mm×2 mm was filled with the dental restorative material, and both surfaces were pressed by glass plates. Thereafter, using a photopolymerization irradiator G-Light Prima (manufactured by GC Corporation), nine locations of the front surface were each irradiated with light for ten seconds to harden the dental restorative material. Next, similarly to the front surface, the back surface was also irradiated with light, and then it was extracted from the mold to obtain a hardened body.

After immersing the hardened body in water of 37° C. for 24 hours, a flexural test was conducted.

Specifically, using a flexural strength testing apparatus autograph (manufactured by Shimadzu Corporation), under conditions of 1 mm/min of a crosshead speed and 20 mm of an inter-fulcrum distance, the flexural test was conducted. At this time, the flexural strength of five hardened bodies was measured, and the average value was obtained.

Smoothness of Hardened Body

A ring-shaped mold was filled with the dental restorative material, and then cover glasses were placed on both surfaces and then it was pressed by glass plates. Thereafter, using a photopolymerization irradiator G-Light Prima (manufactured by GC Corporation), nine locations of the front surface were each irradiated with light for ten seconds to harden the dental restorative material. Next, similarly to the front surface, the back surface was also irradiated with light, and then it was extracted from the mold to obtain a hardened body having a diameter of 15 mm and a thickness of 1.0 mm.

After the hardened body was polished with water-resistant abrasive paper 4000, finishing/polishing was performed by using DIA SHINE (manufactured by GC Corporation), and the gloss of the surface was visually evaluated. It should be noted that the smoothness was determined based on the following criteria.

Excellent: when the gloss of the surface of the hardened body is particularly excellent Good: when the gloss of the surface of the hardened body is good Unacceptable: when the gloss of the surface of the hardened body is inferior Table 1 indicates the evaluation results of the operability of each dental restorative material and the of each dental restorative material.

TABLE 1

| | | HARDENED BODY | |
| --- | --- | --- | --- |
| | OPERABILITY | FLEXURAL STRENGTH [MPa] | SMOOTHNESS |
| Example 1 | EXCELLENT | 155 | EXCELLENT |
| Example 2 | GOOD | 110 | GOOD |
| Example 3 | EXCELLENT | 139 | GOOD |
| Example 4 | EXCELLENT | 150 | EXCELLENT |
| Example 5 | EXCELLENT | 167 | EXCELLENT |
| Example 6 | EXCELLENT | 137 | EXCELLENT |
| Example 7 | GOOD | 129 | EXCELLENT |
| Example 8 | GOOD | 138 | GOOD |
| Example 9 | EXCELLENT | 152 | EXCELLENT |
| Example 10 | EXCELLENT | 151 | EXCELLENT |
| Comparative Example 1 | UNACCEPTABLE | 75 | UNACCEPTABLE |
| Comparative Example 2 | UNACCEPTABLE | 100 | GOOD |

From Table 1, it can be seen that for the dental restorative materials of Examples 1-10, the operability and the flexural strength and the smoothness of the hardened body are high.

In contrast, in the dental restorative material of Comparative Example 1, because the epoxy composition does not contain an epoxide having a (meth)acryloyl group, the operability and the flexural strength and the smoothness of the hardened body are low.

Also, in the dental restorative material of Comparative Example 2, because an epoxy composition containing an epoxide having a (meth)acryloyl group is not used, the operability and the flexural strength of the hardened body are low.

This application is based upon and claims priority to Japanese Patent Application No. 2018-065671, filed on Mar. 29, 2018, the entire contents of which are hereby incorporated herein by reference.

The invention claimed is:

1. A dental filling material that is manufactured by surface-treating an inorganic filling material with a silane coupling agent having an epoxy group and then by causing a ring-opening reaction with a composition containing a ring-opening reaction initiator and containing an epoxide having a (meth)acryloyl group, wherein the ring-opening reaction initiator includes at least one of N,N-diethyl-1,3-diaminopropane, 2,2'-diaminodiethylamine, bis(4-aminophenyl)sulfone or phthalic anhydride.

2. A dental filling material that is manufactured by causing a silane coupling agent having an epoxy group, a composition containing a ring-opening reaction initiator and containing an epoxide having a (meth)acryloyl group, and an inorganic filling material to react, wherein the ring-opening reaction initiator includes at least one of N,N-diethyl-1,3-diaminopropane, 2,2'-diaminodiethylamine, bis(4-aminophenyl)sulfone or phthalic anhydride.

3. A dental polymerizable composition comprising:
the dental filling material according to claim 1 and
a (meth)acrylate.

4. The dental polymerizable composition according to claim 3, wherein the dental polymerizable composition is a dental restorative material.

5. A dental polymerizable composition comprising:
the dental filling material according to claim 2 and
a (meth)acrylate.

6. The dental polymerizable composition according to claim 5, wherein the dental polymerizable composition is a dental restorative material.

7. The dental polymerizable composition according to claim 1, further comprising at least one of a chemical polymerization initiator or a photopolymerization initiator in addition to the ring-opening reaction initiator.

* * * * *